(12) United States Patent
Pradhan et al.

(10) Patent No.: US 8,300,313 B2
(45) Date of Patent: Oct. 30, 2012

(54) METHOD FOR MANUFACTURING AN OPTICAL TRANSMISSION FILTER WITH EXTENDED OUT-OF-BAND BLOCKING

(75) Inventors: Atul Pradhan, Pittsford, NY (US); Jay Anzellotti, Rochester, NY (US); Joseph T. Foss, Rochester, NY (US); Ligang Wang, Rochester, NY (US); Turan Erdogan, Spencerport, NY (US)

(73) Assignee: Semrock, Inc., Rochester, NY (US)

( * ) Notice: Subject to any disclaimer, the term of this patent is extended or adjusted under 35 U.S.C. 154(b) by 0 days.

(21) Appl. No.: 13/097,392

(22) Filed: Apr. 29, 2011

(65) Prior Publication Data

US 2011/0216399 A1    Sep. 8, 2011

Related U.S. Application Data

(62) Division of application No. 11/849,026, filed on Aug. 31, 2007, now abandoned.

(60) Provisional application No. 60/875,359, filed on Dec. 18, 2006, provisional application No. 60/841,552, filed on Sep. 1, 2006, provisional application No. 60/841,551, filed on Sep. 1, 2006.

(51) Int. Cl.
*G02B 5/28* (2006.01)

(52) U.S. Cl. .......... 359/589; 359/359; 359/900

(58) Field of Classification Search .......... 359/350–361, 359/577–590, 900
See application file for complete search history.

(56) References Cited

U.S. PATENT DOCUMENTS

| | | |
|---|---|---|
| 4,142,958 A | 3/1979 | Wei et al. |
| 4,793,908 A | 12/1988 | Scott et al. |
| 6,157,503 A * | 12/2000 | Knapp .......................... 359/830 |
| 6,649,208 B2 | 11/2003 | Rodgers |
| 7,068,430 B1 * | 6/2006 | Clarke et al. .................. 359/589 |
| 7,119,960 B1 * | 10/2006 | Erdogan et al. ............... 359/589 |
| 2004/0027652 A1 * | 2/2004 | Erdogan et al. ............... 359/359 |

OTHER PUBLICATIONS

Jurgen Becker, "Ion Beam Sputtering", Handbook of Optical Properties, vol. 1, Thin Films for Optical Coatings, Ed., by R.E. Hummel and K. H. Huenther (CRC Press, Boca Raton, 1995), pp. 189-212.

J. P. Lehan et al., "Optical and Microstructural Properties of Hafnium Dioxide Thin Films", Thin Solid Films, 203 (1991) pp. 227-250.

H. Angus MacLeod, Thin Film Optical Filters (3rd Ed., Institute of Physics, Bristol, 2001), pp. 46-50 and 500-509.

H. A. MacLeod, "Turning Valve Monitoring of Narrow-Band All-Dielectric Thin-Film Optical Filters," Optica Acta. vol. 19, pp. 1-28 (1972).

Press, W. H. et al., "Numerical Recipies in C: The Art of Scientific Computing", 2nd Ed. , Cambridge University Press, Cambridge, 1995, pp. 683-688.

* cited by examiner

*Primary Examiner* — Thong Nguyen
(74) *Attorney, Agent, or Firm* — Polster Lieder Woodruff & Lucchesi, L.C.

(57) ABSTRACT

In accordance with the invention, a filter is fabricated to take into account the effect of absorption by filter material. The method is exemplified by the fabricating of an ultraviolet light transmission filter for transmitting a band within the range 230-320 nanometers. The resulting filter comprises plurality of hard-coating, thin-film layers of alternating high and low index of refraction. The improved filter provides high transmission, sharp edge slopes, and deep and extended out-of-band blocking. As compared with currently available filters, the filter provides transmission up to three or more times greater, edge slopes up to four times sharper, and deep extended out-of-band blocking extending further, even through the visible range.

19 Claims, 10 Drawing Sheets

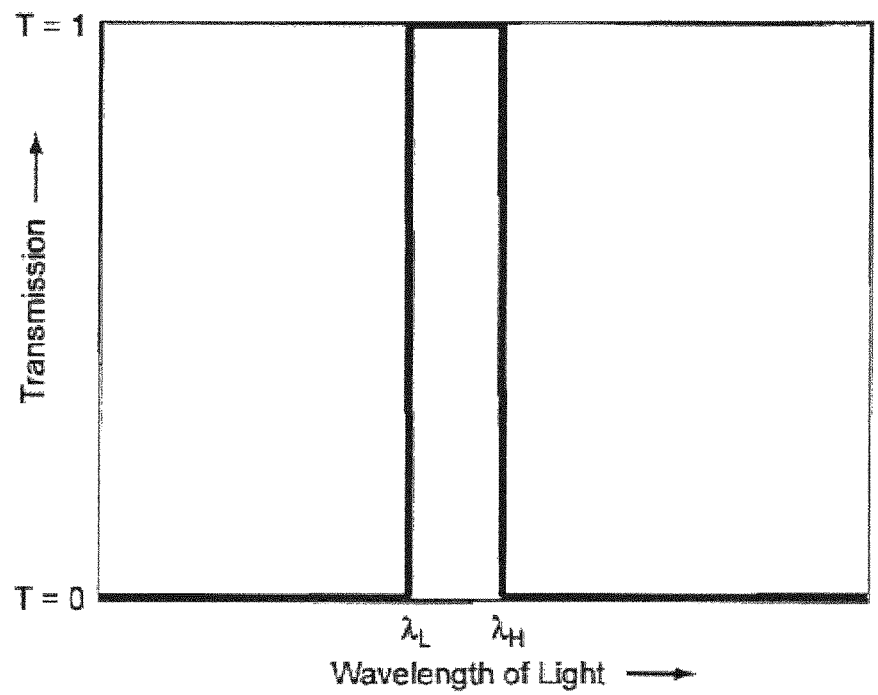
FIGURE 1A - PRIOR ART
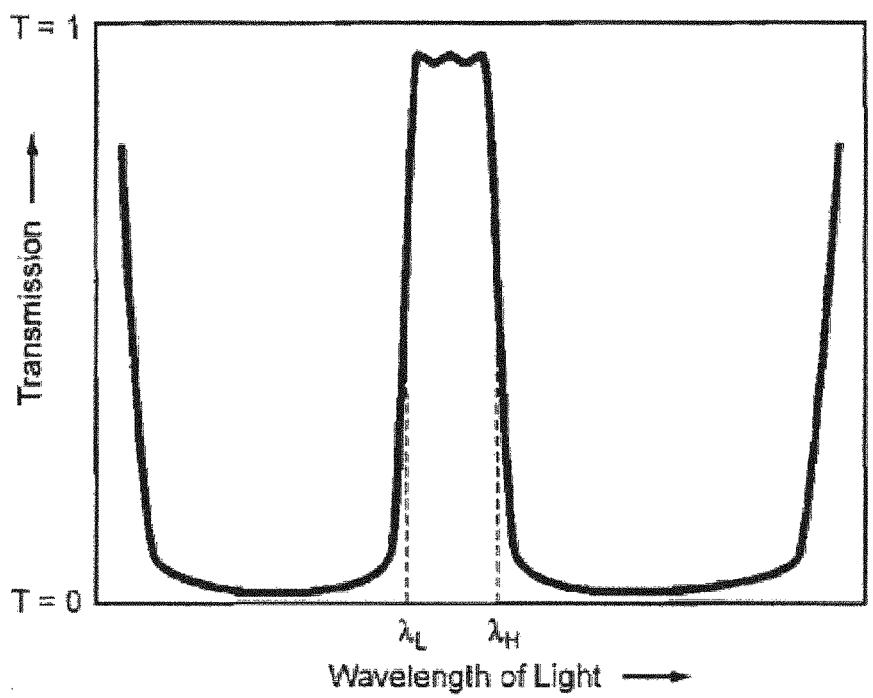
FIGURE 1B - PRIOR ART

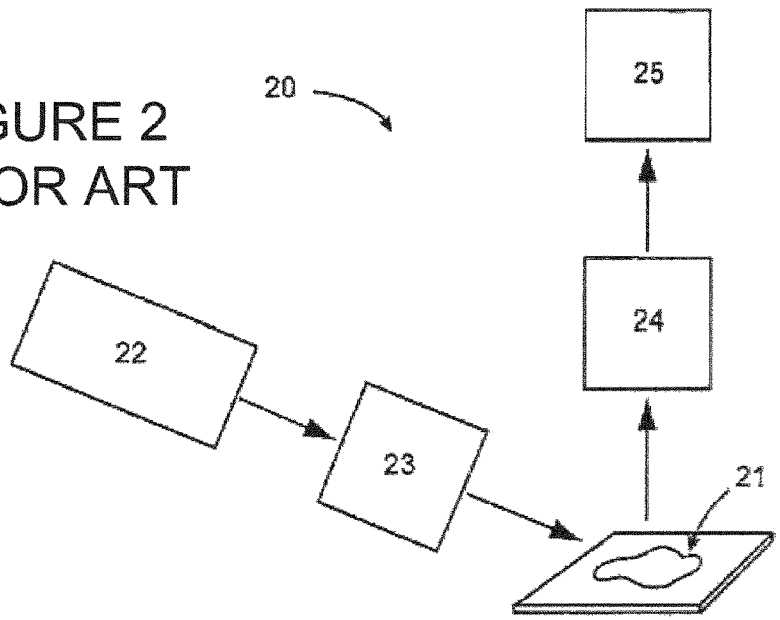
FIGURE 2
PRIOR ART
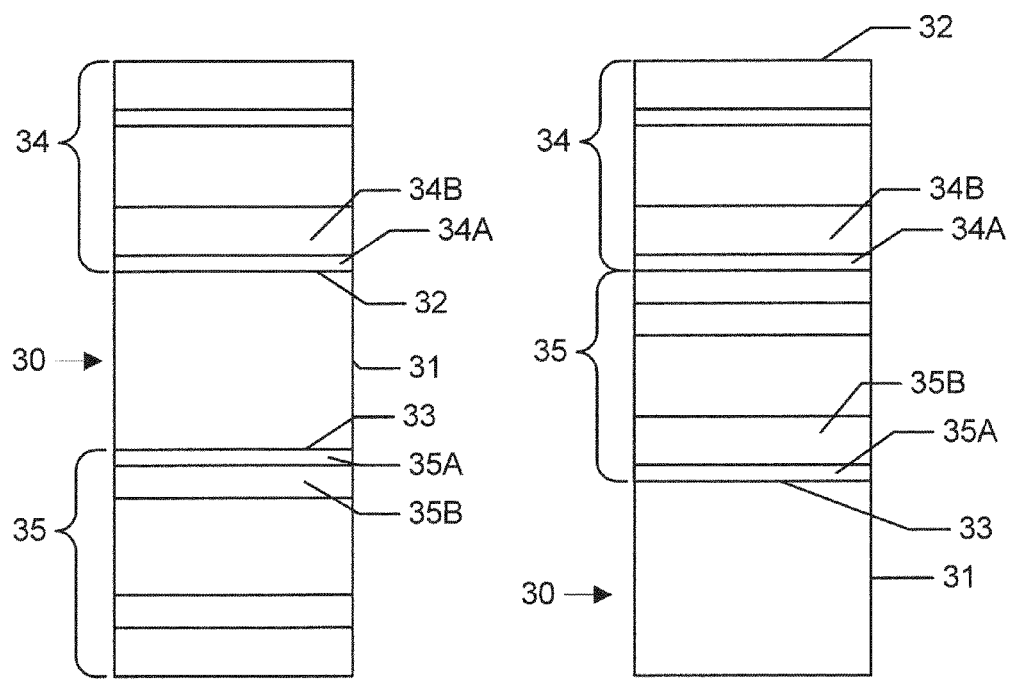
FIGURE 3A
FIGURE 3B

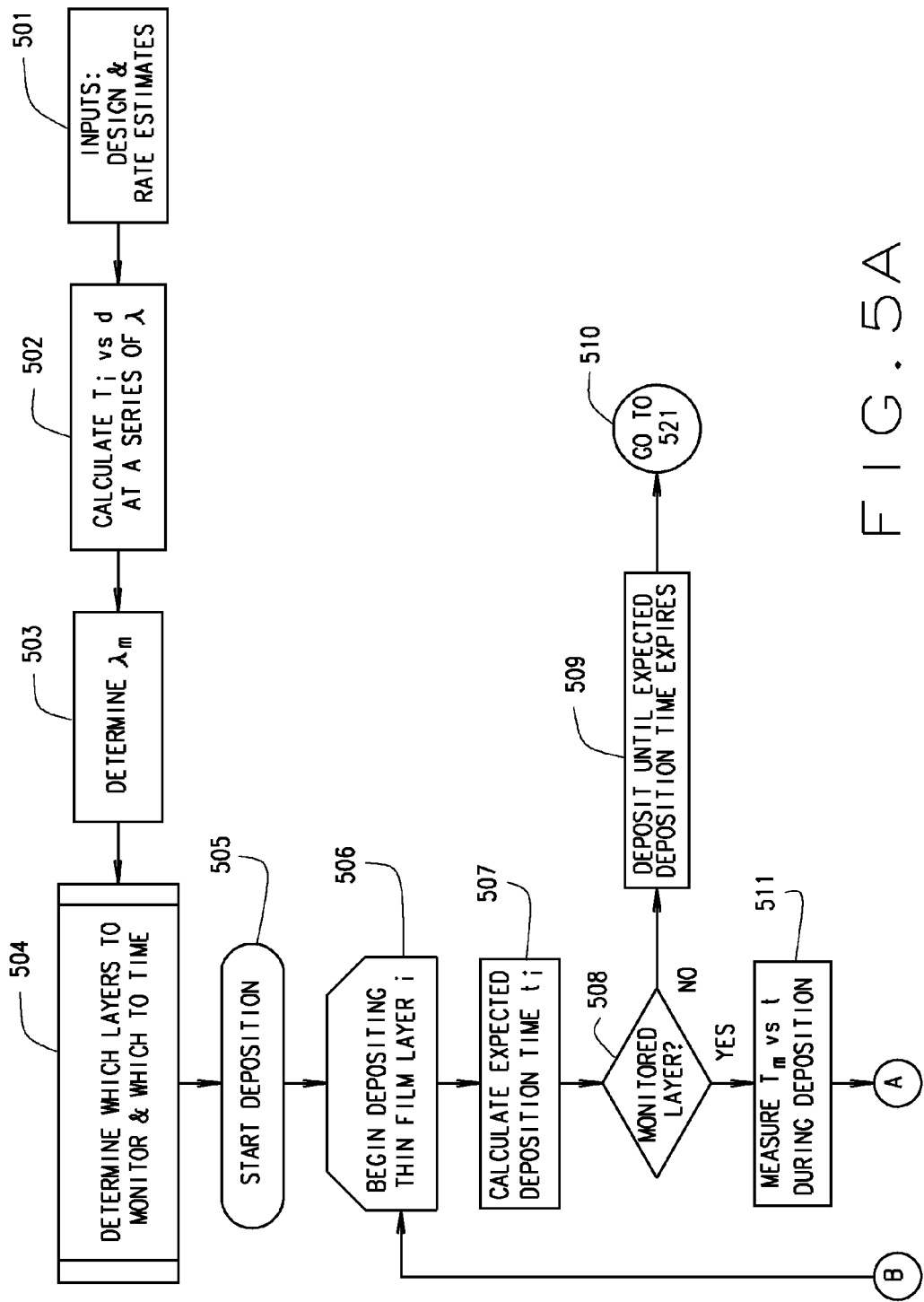

Curve 1 – Linear transmission spectrum (measured):
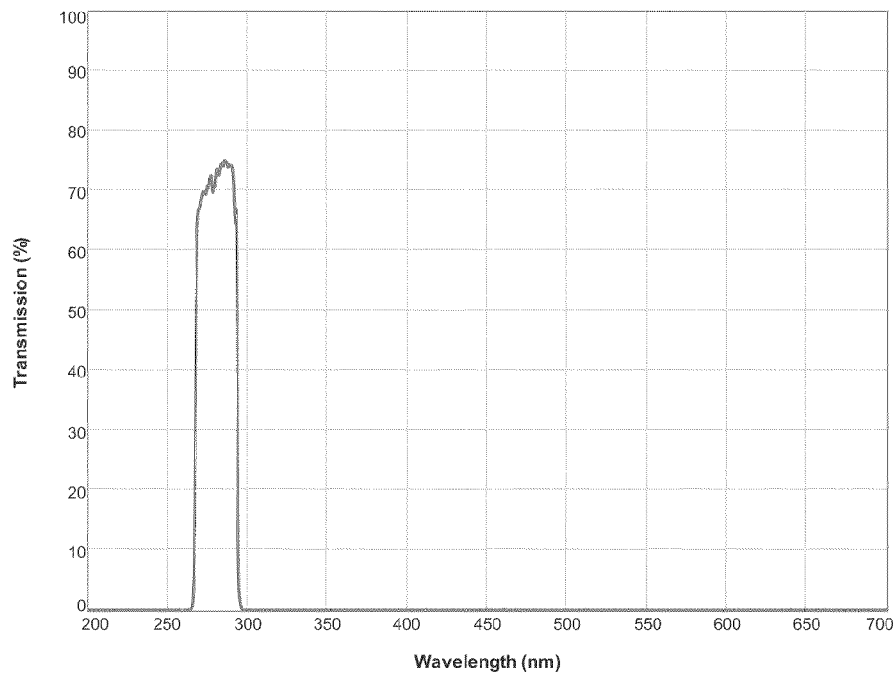
Curve 2 – Linear transmission spectrum (theory):
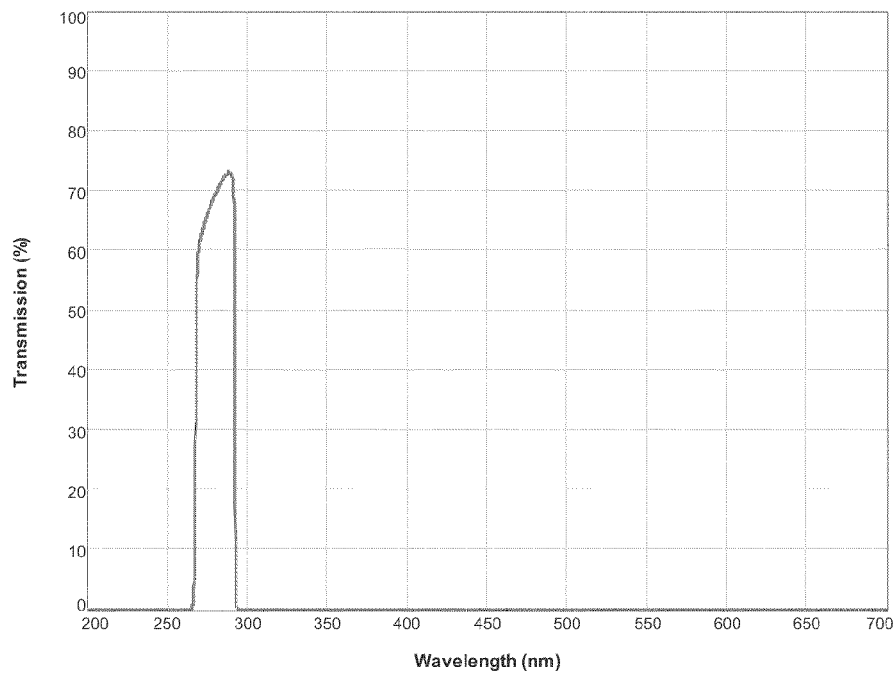
Figure 7

Curve 1 – OD spectrum (measured):
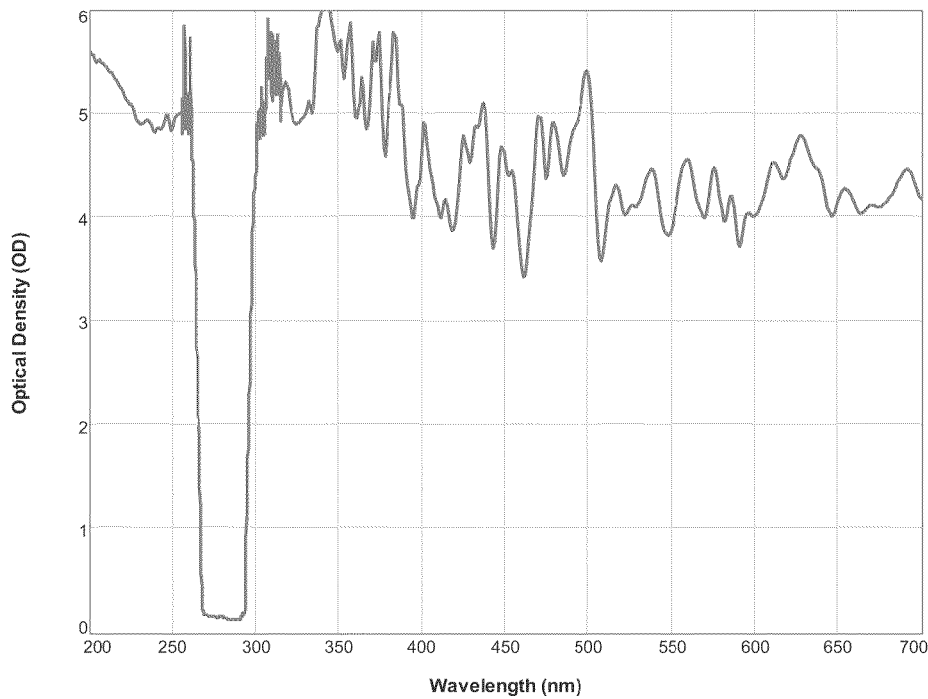
Curve 2 – OD spectrum (theory):
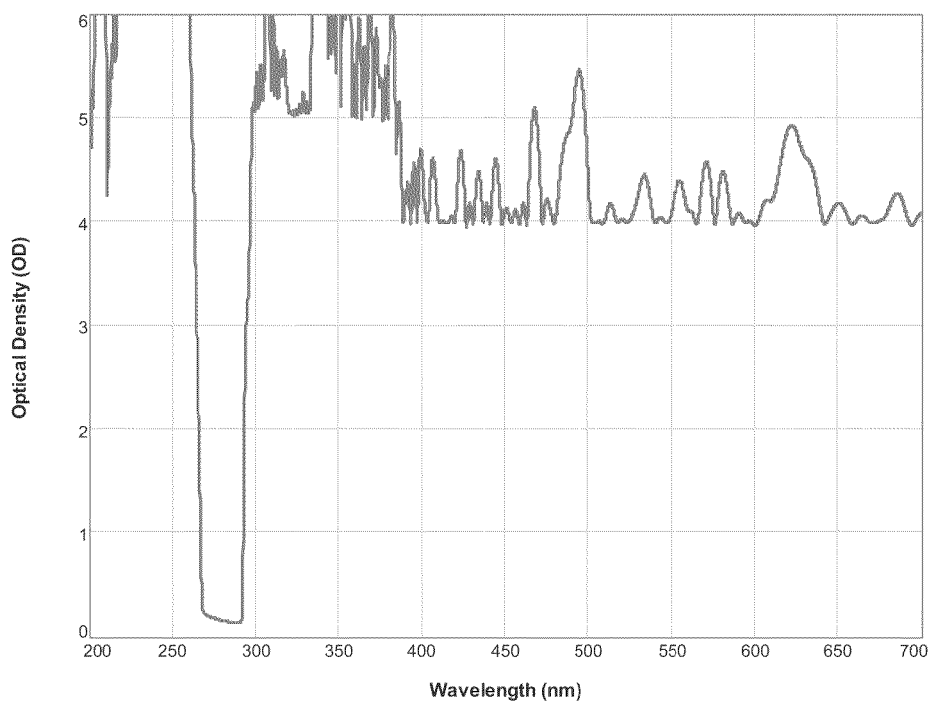
Figure 8

| Wavelength (nm) | In Situ @ 150 °C | | After Annealing @ Room Temperature | |
|---|---|---|---|---|
| | Refractive Index | Extinction Coefficient | Refractive Index | Extinction Coefficient |
| 230 | 2.441 | 5.68E-03 | 2.430 | 1.83E-03 |
| 235 | 2.415 | 3.93E-03 | 2.404 | 1.58E-03 |
| 240 | 2.391 | 2.79E-03 | 2.379 | 1.36E-03 |
| 245 | 2.369 | 2.03E-03 | 2.357 | 1.15E-03 |
| 250 | 2.346 | 1.56E-03 | 2.337 | 9.77E-04 |
| 255 | 2.328 | 1.26E-03 | 2.319 | 8.28E-04 |
| 260 | 2.311 | 1.05E-03 | 2.302 | 7.02E-04 |
| 265 | 2.293 | 9.18E-04 | 2.286 | 5.97E-04 |
| 270 | 2.278 | 8.23E-04 | 2.272 | 5.08E-04 |
| 275 | 2.264 | 7.53E-04 | 2.259 | 4.34E-04 |
| 280 | 2.253 | 6.98E-04 | 2.247 | 3.72E-04 |
| 285 | 2.242 | 6.53E-04 | 2.236 | 3.20E-04 |
| 290 | 2.232 | 6.18E-04 | 2.225 | 2.77E-04 |
| 295 | 2.222 | 5.93E-04 | 2.216 | 2.40E-04 |
| 300 | 2.214 | 5.80E-04 | 2.207 | 2.09E-04 |
| 305 | 2.206 | 5.73E-04 | 2.198 | 1.82E-04 |
| 310 | 2.198 | 5.69E-04 | 2.191 | 1.60E-04 |
| 315 | 2.190 | 5.65E-04 | 2.183 | 1.40E-04 |
| 320 | 2.183 | 5.63E-04 | 2.177 | 1.24E-04 |

Figure 9

METHOD FOR MANUFACTURING AN OPTICAL TRANSMISSION FILTER WITH EXTENDED OUT-OF-BAND BLOCKING

CROSS-REFERENCE TO RELATED APPLICATIONS

The present application claims priority from, and is a divisional of, co-pending U.S. patent application Ser. No. 11/849,026 filed on Aug. 31, 2007, which is herein incorporated by reference. The '026 application in turn claims the benefit of U.S. Provisional Patent Application Ser. No. 60/841,551 filed on Sep. 1, 2006, U.S. Provisional Patent Application Ser. No. 60/841,552 filed on Sep. 1, 2006, and U.S. Provisional Patent Application Ser. No. 60/875,359 filed Dec. 18, 2006, each of which are incorporated herein by reference.

STATEMENT REGARDING FEDERALLY SPONSORED RESEARCH

Not Applicable.

BACKGROUND OF THE INVENTION

This invention relates to optical transmission filters and, in particular, to methods of making improved transmission filters and the resulting improved products and improved equipment that they permit. The invention is particularly useful for filters, such as ultraviolet light filters, for which completely transparent filter materials are not available.

Optical transmission filters are useful in a wide variety of applications including spectroscopy and fluorescence microscopy. Filters are used in these applications to block unwanted light that would otherwise manifest as spurious light that could swamp the signals to be detected or distort the images to be seen.

Optical transmission filters typically transmit a desired range of wavelengths (referred to as a transmission band) and block wavelengths outside the transmission band (out-of-band wavelengths). Ideally they would transmit all light within a desired band and block all light outside the band. In reality, in-band transmission incurs some attenuation and out-of-band blocking is incomplete. Moreover, the spectral extent of blocking is limited, i.e. blocking may substantially diminish for light of wavelengths not far removed from the transmission band.

Referring to the drawings, FIG. 1A schematically illustrates the spectral transmission of an ideal optical transmission filter. An ideal filter would transmit all light having wavelengths within a band between a low wavelength $\lambda_L$ and a high wavelength $\lambda_H$ (the Transmission, T, is equal to 1). An ideal filter would block all light outside the band (T=0). $\lambda_L$ and $\lambda_H$ are the wavelengths at which the filter transitions between blocking and transmitting.

Real filters invariably block a small portion of the light to be transmitted (T<1) and transmit a small portion of the light to be blocked (T>0). Moreover, the blocking may become less effective for wavelengths spectrally away from the transmission band. These properties are schematically illustrated in FIG. 1B showing the effect of a filter with less than perfect transmission, finite transition regions, less than perfect blocking, and out-of-band transmission. The proportion of light transmitted, the steepness of the transition lines and the extent of the blocking are important parameters in many applications.

Transmission filters are particularly important in optical measurement and analysis systems. Some such systems, e.g. fluorescence systems, use light of one wavelength to excite a sample of material and then measure or view an optical response of the excited sample at another wavelength. The excitation light is delivered to the sample by an excitation light path, and the optical response of the sample is delivered to the eye or measuring instrument by a collection path. Transmission filters between the source and the sample can be used to block spurious light from the excitation path. The steeper the filter transition lines, the more effectively spurious signals are blocked. The lower the transmission loss, the more light from the desired excitation band reaches the sample. Moreover, if the optical response being measured differs considerably in wavelength from the excitation light, the transmission filter needs extended out-of-band blocking to prevent transmission of spurious light that can scatter into the collection path.

UV fluorescence spectroscopy is based on the fact that when some materials are excited by ultraviolet light (light that is composed of wavelengths too short to be visible) they respond by the emission of near-UV and/or visible light ("fluorescent light"). In such apparatus it is important that the UV excitation path not transmit visible light that can also be transmitted as a spurious signal through the collection path.

FIG. 2 is a simplified schematic diagram of a UV probe 20 designed to excite a sample 21 by UV light and to collect visible fluorescent light from the sample. In essence, the probe comprises a UV source 22, an excitation path 23 for transmitting the UV light to the sample 21 and a collection path 24 for transmitting the fluorescent response light from the sample 21 to a detector 25. The excitation path 23 for UV light ideally transmits only UV light that will excite specific materials ("markers") in the sample. In reality, UV light sources may include or can generate spurious visible light by a number of mechanisms. The spurious visible light can scatter off the sample 21 into the collection path 24 to the detector.

Absorption spectroscopy is another optical analysis technique used in identifying materials and quantifying concentrations. In absorption spectroscopy light of one or more discrete bandwidths is transmitted through a first path and through a sample. Light from the illuminated sample is transmitted through a collection path to a detector that can measure the amount of light the sample absorbed. The amount of absorption provides information regarding the identity of unknown materials or the concentration of known materials. Spurious light through the first path can provide incorrect or inaccurate results.

It should be clear that the steeper the filter slope at the transition wavelengths $\lambda_L$, $\lambda_H$, the greater the amount of unwanted light that can be filtered out, avoiding spurious results. The greater the in-band transmission of the filter, the greater the input of desired light. And the greater the extent of out-of-band blocking, the less spurious light at the output to interfere with measurement or viewing.

Systems using UV excitation light, particularly UV bands in the wavelength range 230 to 320 nanometers, are particularly useful. The term "bands within the wavelength range" as used herein is intended to include smaller wavelength bands included within the range, e.g. 250-270 nanometers, as well as bands that encompass the range, e.g. 220-325 nanometers. Bands within the 230-320 wavelength range have attained prominence for use in biomedical applications as diverse as drug discovery, genomics and proteomics, immunology, chemical process tracing and threat biodetection. UV bands in this range are highly useful in the fluorescent detection of nucleotides, proteins and enzymatic molecules.

Unfortunately existing filters and equipment leave much to be desired for bands within the 230 to 320 nanometer range.

Few commercial filters are available in the range, and none provide the combination of high transmission, steep edge slopes and deep, extended out-of-band blocking needed for high performance detection and measurement.

Typical commercial filters are metal-dielectric filters and soft-coating thin film filters. Metal-dielectric filters provide relatively low transmission: typically only 10-30%. The low-transmission in such filters is inherent because transmission performance is inversely related with achievable blocking.

"Soft-coating" thin-film filters, as well as those that achieve partial blocking using colored absorbing glasses, are not suitable for high intensity light sources in the 230-320 nanometer range. In the UV range, soft-coating materials suffer from severe reliability, durability and spectral stability issues. Even moderate amounts of illumination by high intensity UV sources can cause soft coatings and colored substrates to "burn out", solarize or photodarken.

A new approach to making highly discriminating optical filters and the resulting improved products are disclosed in U.S. Pat. No. 7,068,430 which is incorporated herein by reference. This approach offers considerable promise for application to filters for the visible range where essentially transparent materials are available. The present invention is an extension and modification of the '430 method to produce advantageous filters for shorter wavelengths where completely transparent materials are not available.

BRIEF SUMMARY OF THE INVENTION

In accordance with the invention, a filter is fabricated by a modified form of the process disclosed in U.S. Pat. No. 7,068,430. In particular, the method is modified to take into account the absorption of short wavelengths by filter material. The method is exemplified by the fabricating of an ultraviolet light transmission filter for transmitting a band within the range 230-320 nanometers. The resulting filter comprises plurality of hard-coating, thin-film layers of alternating high and low index of refraction. The improved filter provides higher transmission, sharper edge slopes, and deeper and extended out-of-band blocking. As compared with currently available filters, the filter provides transmission up to three or more times greater, edge slopes up to four times sharper, and deep out-of-band blocking extending into and even through the visible range.

The foregoing features, and advantages set forth in the present disclosure as well as presently preferred embodiments will become more apparent from the reading of the following description in connection with the accompanying drawings.

BRIEF DESCRIPTION OF THE SEVERAL VIEWS OF THE DRAWINGS

In the accompanying drawings which form part of the specification:

FIGS. 1A and 1B are schematic illustrations of the spectral transmission of ideal and real optical transmission filter;

FIG. 2 is a simplified schematic diagram of a UV probe to excite and collect optical fluorescence from a sample;

FIG. 3 schematically illustrates an improved optical transmission filter

FIGS. 5A and 5B illustrate a process flow chart for making the long-wave pass component of a filter;

FIG. 7 is a graphical illustration of the theoretical and measured transmission spectra of a exemplary filter;

FIG. 8 illustrates the optical density spectrum of the exemplary filter; and

FIG. 9 is a table giving the index of refraction for $HfO_2$ at wavelengths of interest.

Corresponding reference numerals indicate corresponding parts throughout the several figures of the drawings. It is to be understood that the drawings are for illustrating the concepts set forth in the present disclosure and are not to scale.

Figure 4:
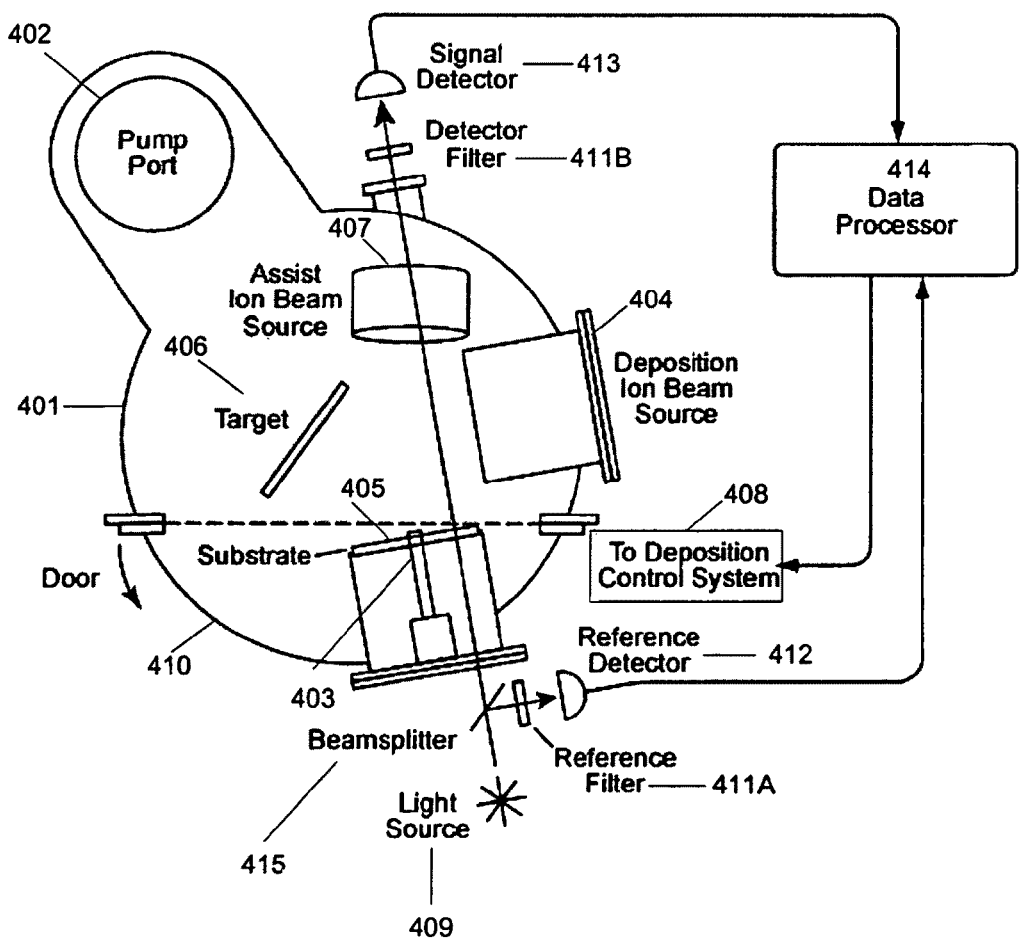
FIG. 4 is a schematic view of a computer-controlled deposition apparatus useful in making filters.

Before any embodiments of the invention are explained in detail, it is to be understood that the invention is not limited in its application to the details of construction and the arrangement of components set forth in the following description or illustrated in the drawings.

BRIEF DESCRIPTION OF THE APPENDIX

The accompanying Appendix A, which forms part of the specification, sets forth layer thicknesses in an exemplary filter manufactured according to the methods of the present disclosure.

DETAILED DESCRIPTION

The following detailed description illustrates the invention by way of example and not by way of limitation. The description enables one skilled in the art to make and use the present disclosure, and describes several embodiments, adaptations, variations, alternatives, and uses of the present disclosure, including what is presently believed to be the best mode of carrying out the present disclosure.

Referring to the drawings, FIG. 3 schematically illustrates an improved optical transmission filter. The filter 30 comprises a substrate 31 having one or more surfaces 32 and 33 for supporting thin film hard coatings. The support surfaces 32, 33 are typically opposing optically smooth, planar major surfaces of a thin substrate. The hard coatings forming the transmission filter (e.g. interference filter components 34, 35) can overlie respective surfaces 32, 33 or they can both overlie the same surface. See: U.S. Provisional Patent Application 60/841,552 incorporated herein by reference. In the embodiment illustrated a first interference filter component 34 is disposed overlying a first surface 32 and a second interference filter component 35 is disposed overlying the second surface 33. The first filter component 34 comprises alternating layers 34A, 34B of at least two materials of relatively higher refractive index (34A) and relatively lower refractive index (34B), respectively, to form a long wavelength pass filter component that transmits the passband wavelengths but blocks wavelengths below the passband. The second filter component 35 comprises alternating layers 35A, 35B of at least two materials of relatively higher refractive index (35A) and relatively lower refractive index (35B) to form a short wavelength pass filter component that transmits the passband wavelength but blocks wavelengths above the passband. The first and second filter components thus cooperate to transmit light within the passband and to block light outside the passband. One or both of the materials may be materials that absorb small, but not negligible, amounts of light within the passband wavelengths.

In a preferred embodiment, the filter 30 has a passband of ultraviolet light within the range of 230 nanometers to 320 nanometers. The substrate 31 is substantially transparent to ultraviolet light, and the first and second interference filters 34, 35 comprise hard coatings of non-metals that may absorb small amounts of ultraviolet light. Typically, the filters 34, 35 each comprise 30 or more alternating layer pairs. The substrate is advantageously fused silica or calcium fluoride, and the coatings preferably comprise alternating layers of silica and hafnia.

The improved filters described herein are advantageously made by a data processor-controlled deposition system. The preferred deposition system is an ion beam sputtering deposition system using an ion beam assist source for depositing hard coatings combined with an integral optical monitoring system for monitoring deposition. A data processor, responsive to signals from the monitoring system, processes the signals and directs the growth of the layers.

FIG. 4 is a schematic view of an advantageous data processor-controlled deposition apparatus 400 for making the filter by ion beam sputtering disposition with optical monitoring under data processor control. The apparatus 400 comprises a vacuum chamber 401 having an interior accessible by a sealable port 402 such as an o-ring sealed door. The chamber 401 includes a pump port 402 for coupling to one or more evacuating pumps (not shown) such as mechanical and low pressure cryogenic pumps.

Within the chamber 401 is a substrate mount 403 which is advantageously a rotatable spindle mount. Also within the chamber are a plurality of material targets, a deposition ion beam source 404, and a mounted substrate 405. One of the targets 406 is positioned in relation to the ion beam source and the substrate so that an ion beam from the source will sputter material from the target onto the substrate in a substantially uniform layer. Typically there are separate targets for each material to be deposited on the substrate, and the targets are moveable to and from the sputtering position. There are usually two material targets: one for depositing a high optical index material, such as hafnia ($HfO_2$), and the other for depositing a low index material, such as silica ($SiO_2$). The targets are moveable so that deposition can be switched automatically from one material to the other. An Hf metal target can be used during the hafnia deposition and is preferably chosen to have Zr contamination of less than 0.8%.

An assist ion beam source 407 is disposed in the chamber 401 in position to bombard the substrate 405 with an ion beam. Normally during the deposition of any one material, the substrate is simultaneously bombarded by sputtered material and by ions from the assist ion beam source 407. See: J. M. E. Harpe et al., "Modification of Thin Film Properties by Ion Bombardment During Deposition," in Ion Bombardment Modification of Surfaces, Ed. by O. Auciello and R. Kelly, from Beam Modification of Material, Vol. 1 (Elsevier, Amsterdam, 1984).

In the preferred embodiment of this invention using hafnia and silica, the assist ion beam is turned off during the deposition of hafnia ($HfO_2$) and turned on during the deposition of silica ($SiO_2$). The use of the assist beam during hafnia ($HfO_2$) deposition results in films with undesirably high crystallinity, absorption (due to hafnia layers with extinction coefficient $>1\times10^{-3}$), and scatter. We have further found that an important factor for reducing the UV extinction in thin films of both hafnia and silica is the regulation of flow of $O_2$ into the deposition chamber. The rate of $O_2$ injection during deposition determines the stoichiometry of the hafnia and silica layers. In particular, the formation of $HfO_2$ in the hafnia layer from Hf metal precursor atoms and $O_2$ molecules has a profound effect on the absorption characteristics of the film. The optimum stoichiometry is achieved with a flow of 12 sccm of $O_2$ of which 6 sccm are from the target $O_2$, and 6 sccm from the ion source. These flow settings achieve hyperstoichiometric hafnia thin films with reduced UV absorption.

Both the sputter deposition and the assist bombardment can be activated by a deposition control system 408. The control system 408 can start or stop deposition precisely by turning on and off the deposition ion beam source 404 or by removing or engaging a mechanical shutter (not shown) that covers the substrate. Further details concerning ion beam sputtering deposition systems can be found in U.S. Pat. No. 4,142,958 issued to David Wei et al. on Mar. 6, 1979 and U.S. Pat. No. 4,793,908 issued to Gene Scott et al. on Dec. 27, 1988, both of which are incorporated herein by reference. See also Juergen Becker, "Ion Beam Sputtering," Handbook of Optical Properties, Vol. 1, Thin Films for Optical Coatings, Ed., by R. E. Hummel and K. H. Guenther (CRC Press, Boca Raton, 1995).

The above depositional process produces low absorption hafnia layers. The hafnia ($HfO_2$) material layers exhibit a small extinction coefficient of $<5\times10^{-4}$ leading to low absorption. This low extinction coefficient correlates with a realized O(Oxygen) to Hafnium (Hf) atomic ratio greater than 2.0 (hyperstoichiometry) in the hafnia layers.

It is believed that the presence of excess oxygen in the hyperstoichiometric hafnia ($HfO_2$) reduces optical absorption by quenching dangling bonds in the amorphous-crystalline hafnia ($HfO_2$) layer mixture. Such hyperstoichiometry ($N(O)/N(Hf)=2.16$) in hafnia layers is also confirmed by a low oxygen to hydroxide ratio (in this case $N(O)/N(OH)=1.37$) since a correlation of hyperstoichiometry with a oxygen/hydroxide ratio is reported in a previous E-beam evaporated hafnia thin-film study (Optical and Microstructural Properties of Hafnium Dioxide Thin Films, J. P. Lehan, Y. Mao, B. G. Bovard, and H. A. Macleod, Thin Solid Films, 203 (1991) pp 227-250).

In the advantageous arrangement shown here, a beam splitter 415 picks off a portion 416 of the monitoring light beam 417 from source 409 and detects it with reference detector 412. The signal detector 413 detects the portion 418 of the beam 417 that passes through the coated substrate (or a "witness" substrate) being monitored. Advantageously, the filters 411A and 411B are positioned to ensure that a sufficiently narrow band of wavelengths is monitored.

The filters 411A, 411B can be narrow band interference filters, adjustable diffraction-grating monochromators or combinations thereof. Further details concerning optical monitoring of thin films as they are being deposited can be found in U.S. Pat. No. 6,649,208 issued to Wayne Rodgers on Nov. 18, 2003, which is incorporated herein by reference. See also: H. Angus Macleod, Thin Film Optical Filters ($3^{rd}$ Ed., Institute of Physics, Bristol, 2001) and H. A. Macleod, "Turning Value Monitoring of Narrow-Band All-Dielectric Thin-Film Optical Filters," Optica Acta. Vol. 19, pp. 1-28 (1972).

The data processor 414 collects data from the signal and reference detectors 413, 412, implements the mathematics associated with optical monitoring algorithms and instructs the deposition control system 408 when to stop depositing any given thin film layer based on the result of the mathematical calculations prescribed by algorithm.

The manner in which the data processor 414 controls the apparatus 400 via the deposition control system 408 to generate the optical filters according to the present invention will now be described. In particular, the data processor 414 is programmed to instruct the apparatus 400 when to stop depositing each layer of the optical filter being manufactured. The data processor 414 follows two separate processes in determining when a deposition of a layer should terminate depending upon whether a long-wave-pass component or a short-wave-pass component is being manufactured. These two processes will be described in turn.

Figure 5B:
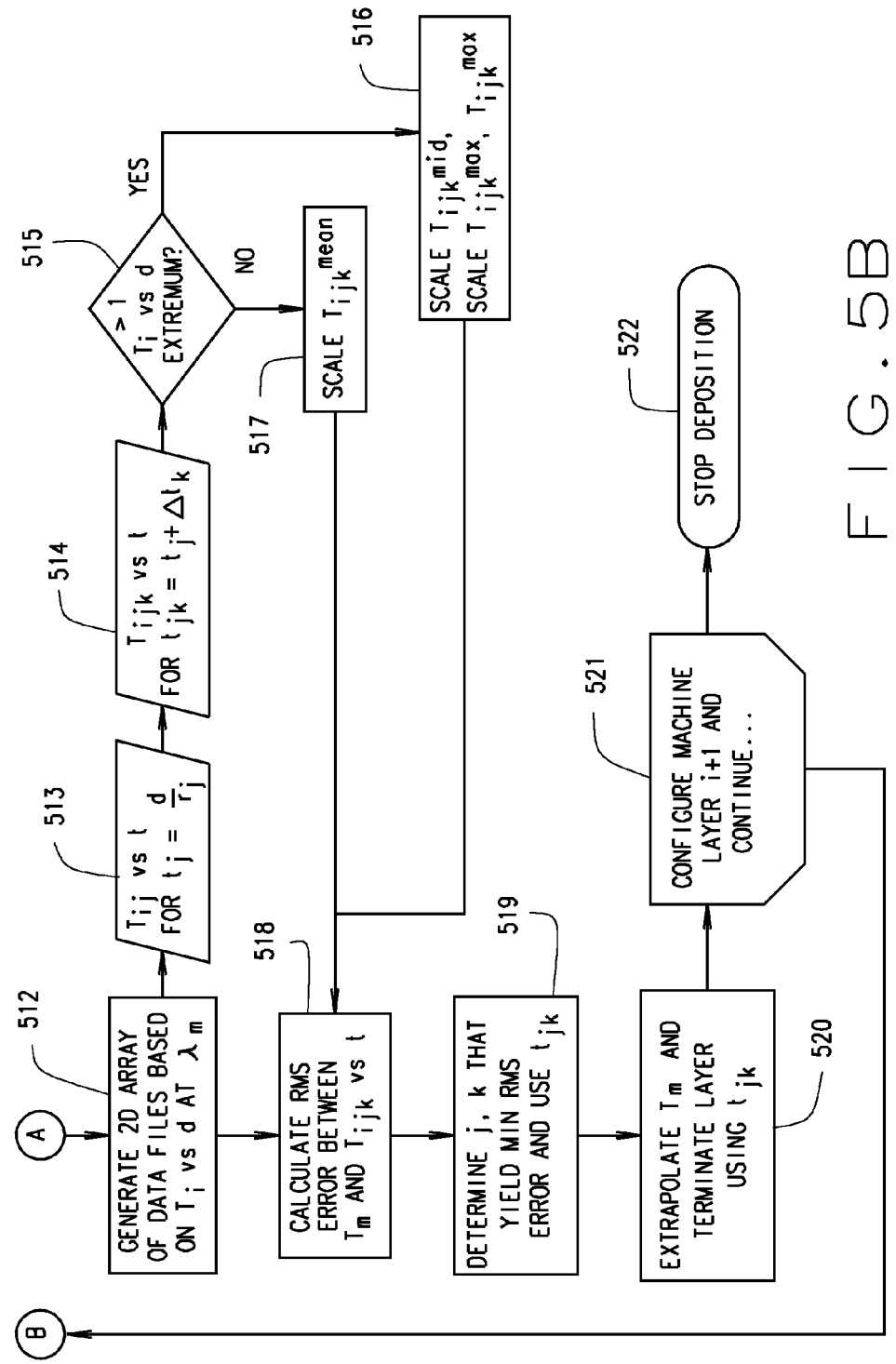

FIGS. 5A and 5B illustrate the process flow executed by the data processor 414 when manufacturing a long-wave-pass ("LWP") filter component. However, prior to initiating the process of FIGS. 5A and 5B, a design for the LWP filter is prepared. In the exemplary embodiment, the LWP filter has N layers (typically $n \geq 30$) and comprises at least two materials: a relatively lower-refractive-index material and a relatively higher-refractive-index material. The exemplary initial design for a steep LWP edge filter includes a quarter-wave ("QW") stack of $(0.5H\ L\ 0.5H)^N$ where L and H represent layers of high and low index materials with a quarter-wave of optical thickness at the reference wavelength. The reference wavelength is chosen so that the longer-wavelength edge of the QW stopband is close to the desired transition wavelength of the LWP filter component.

Once the initial design is setup, a desired target spectrum is constructed, which typically includes the wavelength ranges of both the blocking and passband regions, as well as the required blocking level and minimum transmission and allowable ripple within the passband. The edge steepness is thus indirectly defined as the wavelength separation between the blocking region and the passband.

The layer thicknesses of the initial design are then optimized against the target spectrum by an optimization routine known in the art. Exemplary optimization routines include the variable-metric or simplex methods implemented in standard commercial thin-film design software packages, such as TFCalc by Software Spectra, Inc., and The Essential Macleod by Thin Film Center Inc. Usually, with the proper choice of the initial design, the optimization quickly converges and the optimized structure is not very different from the initial structure. Special treatments are required for the first layer (toward substrate) and the last layer. The metric thickness of the first layer should be required to meet a minimum thickness threshold, typically 10 nm, in order for robust control by the optical monitoring algorithm. As for the last layer, it sometimes becomes too thin and, consequently, should be eliminated. The structure should be re-optimized whenever there is any modification to the layer thickness.

In preparing the initial design of the long wave pass filter component, it is important to take into consideration the effect of fabrication conditions on the applied layers. The indices of refraction of the applied materials, particularly in UV long wave pass filters, are functions of temperature, pressure and thermal treatment. Here the materials are coated on a substrate typically held at an elevated temperature (roughly 150° C.) in a near vacuum atmosphere. Moreover the deposited materials are, after deposition, typically finished by annealing (baking) them at an elevated temperature for several hours—typically 425° C. for 2-4 hours. The result is that the index after fabrication is different than the index during fabrication. In general, this difference is very small for coatings used in visible light filters and can usually be ignored as negligible. But in UV filters the difference is somewhat larger and should be considered in the initial design, as it affects the optical monitoring process during filter fabrication. Specifically, the coating indices during fabrication should be targeted so that the final indices after deposition, annealing and cooling will be indices desired.

In making the present filters $HfO_2$ is the material most sensitive to fabrication conditions. The correlation at different wavelengths between the index during deposition ("in situ") and the index at room temperature after annealing is given in the Table set forth as FIG. 9. The indices are specified as complex indices of refraction with the "real part" being the Refractive index and the "imaginary part" being the extinction coefficient. Values for wavelengths not listed may be determined sufficiently accurately by interposition. The variation of the index for $SiO_2$ is not significant for this filter.

In application, the design created uses the after annealing index values. The calculations that are part of the fabrication monitoring process use the "in situ" values so that the end result is in accordance with the design.

With the LWP filter design at hand, the data processor 414 receives design data and deposition rate data as input at 501. The design data describes the designed thin-film structure of the LWP filter with a physical thickness $d_i$ and an index $n_i$ for each $i^{th}$ layer. $n_i$ is either $n_L$ or $n_H$, where $n_L$ is the refractive index of the low-index material and $n_H$ is the refractive index of the high-index material. $n_L$ and $n_H$ are each known as a function of wavelength $\lambda$. The deposition rate data describes the known starting deposition rate of the deposition apparatus 400 shown in FIG. 4 for each of the two materials. In the exemplary embodiment, the deposition rate data is within about +/−5% of the actual deposition rate and is in units of Å/sec. The starting rate estimates for each of the two materials are referred to as $r_L$ and $r_H$, and hence each layer will have a starting rate estimate $r_i$ depending on whether it is made of low-index or high-index material.

At 502, the transmission $T_i$, as a function of physical thickness d for each $i^{th}$ layer is calculated at a series of wavelengths in the transmissive band of the finished filter. Consequently, the calculations at 502 result in a series of curves $T_i$ vs. d at each of the series of wavelengths in the transmissive band of the finished filter. Such calculations are performed using standard mathematical methods for calculating the optical properties of thin-film filters. See, for example, H. A. Macleod, Thin-film Optical Filters, 3rd edition (Institute of Physics, Bristol, 2001).

Advantageously, instead of calculating each $T_i$ vs. d curve at one corresponding wavelength in the series of wavelengths, each $T_i$ vs. d curve is calculated by averaging a plurality of $T_i$ vs. d curves calculated at a range of wavelengths surrounding the corresponding wavelength. For instance, assume that the series of wavelengths includes 241 nm and 242 nm. Instead of calculating a $T_i$ vs. d curve at just 241 nm, this $T_i$ vs. d curve is advantageously calculated by averaging $T_i$ vs. d curves calculated at, for instance, 240 nm, 241 nm, and 242 nm. Further, the $T_i$ vs. d curve at 242 nm is advantageously calculated by averaging $T_i$ vs. d curves calculated at, for instance, 241 nm, 242 nm, and 243 nm. One skilled in the art will appreciate that invention is not limited to this averaging procedure and the range of wavelengths used.

At 503, an optical monitoring wavelength $\lambda_m$ is selected from the series of wavelengths in the transmissive band of the finished filter, thereby identifying a single curve $T_i$ vs. d at $\lambda_m$, from the series of curves computed at 502. The monitoring wavelength $\lambda_m$, is determined based on the contrast of the monitoring signal within each layer. The contrast is defined as the relative range of the monitoring signal within the layer of interest. The higher the contrast, the more robust the process flow of FIGS. 5A and 5B will be with respect to random signal noise.

Advantageously, the relative separation between the monitoring and cutoff wavelengths should be at least about 2%. Once above 2%, the monitoring wavelength $\lambda_m$ should be chosen to maximize the contrast of each layer. In addition, the optical thickness of the first layer toward the substrate has a significant impact on the signal contrast for the rest of the coating. Therefore, the optical thickness of the first layer should be close to three quarter-wavelengths at the monitoring wavelength $\lambda_m$.

Having determined the monitoring wavelength $\lambda_m$ at 503, processing advances to 504 where it is determined how the deposition duration for each layer will be calculated. For layers that are predicted to have little error between the designed thickness d and a simulated actual thickness, deposition duration is controlled by optically monitoring transmission levels $T_m$ through the layer during deposition. For the other layers, their deposition durations are controlled using an expected deposition time $t_i$ based upon designed ("theoretical") thickness $d_i$ and deposition rate $r_i$. Accordingly, at 504, the data processor 414 determines which layers are to be optically monitored and which layers are to be timed using an expected deposition time.

To determine which layers will be optically monitored, the data processor 414 enters a simulation mode to simulate deposition of each of the layers of the optical filter. Only the layers 25 that are determined by the simulation to have the least amount of error are selected for optical monitoring. The simulation mode is nearly identical to the process described below with reference to 505 to 522, except that layers are not actually deposited at 505 and 506, the processing described at 508 is skipped, and instead of actually measuring transmission data $T_m$ vs. t at 511, it is generated. $T_m$ vs. t is generated by adding random noise to the theoretical data $T_i$ vs. d at $\lambda_m$ from 502 and 503. In the exemplary embodiment, 0.2% peak-to-peak random noise is used, and the maximum amount of error ("threshold") to select a layer for optical monitoring is to have no more than about 0.2% error from the theoretical thickness $d_i$. The error calculation, in this regard, is discussed in more detail below with reference to 518 and 519. The layers that are simulated to exceed the threshold amount of error are flagged to have their deposition duration controlled by the best estimate of the deposition rate $r_i$ for that layer or from an average of the rates of the previous layers of like material (typically 10 to 20 of such layers).

After determining which layers are to be optically monitored at 504, actual deposition of the layers of the LWP filter begins at 505. In particular, the substrate is loaded into the deposition apparatus 400 of FIG. 4, the apparatus is pumped down to a vacuum, and deposition of the first layer (current layer i) is initiated at 506. The expected deposition time $t_i$ for layer i is calculated as the desired thickness $d_i$ divided by the estimated deposition rate $r_i$ for the layer or from an average of the rates of the previous layers of like material at 507. It should be noted, however, that calculation of the expected deposition time $t_i$ at 507 may be calculated prior to beginning actual deposition of the current layer i at 506.

After calculating the expected deposition time $t_i$, it is determined whether the current layer i has been identified as a layer to be optically monitored for controlled deposition duration. If the current layer has not been so identified, deposition of the current layer terminates when the expected deposition time $t_i$ from 507 expires, as shown at 509. After the expected deposition time $t_i$ has expired, processing advances to 521 where the next layer is queued up for deposition, as shown at 510.

If it is determined at 508 that the current layer i is to be optically monitored, the actual transmission $T_m$ is measured at 511 as a function of actual time transpired t until about 95% of the expected deposition time $t_i$ has elapsed. Once about 95% of $t_i$ has elapsed, a new deposition duration is calculated at 512-520. In particular, at 512, 513, and 514, using the $T_i$ vs. d at $\lambda_m$ curve from 502 and 503, a two-dimensional (2D) array of additional curves is generated by plotting the values of $T_i$ against a 2D array of time vectors $t_{jk}$. In particular, at 513, transmission $T_{ij}$ is generated by plotting $T_i$ against the values $t_j = d/r_j$ where $r_j$ represents, for each j, a deposition rate having a value close to the predicted value $r_i$. That is, the set of all $r_j$ values is a range of values surrounding the predicted value $r_i$. Accordingly, j is an index that counts the number of r values that come from the range surrounding the predicted value $r_i$. At 514, for each value of j, transmission $T_{ijk}$ is generated by plotting $T_{ij}$ against the values $t_{jk} = t_j + \Delta t_k$, where $\Delta t_k$ represents various values used for a uniform time shift.

At 515, it is determined whether there is more than one extremum in the curve $T_i$ vs. d at $\lambda_m$. If there is more than one extremum at 515, then each of the 2D array of curves generated at 512-514, is scaled in two ways at 516. First, the mid-point between the two extrema for each $T_{ijk}$ curve is scaled by a factor so that it equals the mid-point between the two extrema of the measured data $T_m$ vs. t. Second, the maximum and minimum values on each $T_{ijk}$ curve are scaled by scaling uniformly about their mean so that the difference between the maximum and minimum for each curve $T_{ijk}$ is the same as that on the measured curve $T_m$ vs. t. If there is one or no extremum at 515, then the mean of each $T_{ijk}$ curve is scaled at 517 by a uniform factor so that it is equal to the mean of the measured curve $T_m$ vs. t.

After scaling at 516 or 517, processing advances to 518 where error is calculated. For each of the 2D array of generated $T_{ijk}$ curves, the root-mean-square (RMS) error between each $T_{ijk}$ curve and the measured curve $T_m$ vs. t is computed. Typically this computation is performed only for data between about 10% and 95% of the expected deposition time $t_i$. Afterwards, the values of j and k that yield a minimum RMS error at 518 are identified at 519. Therefore, the curve $T_{ijk}$ vs. $t_{jk}$ is taken to be the best approximation of the actual curve $T_m$ vs. t for layer i. At 520, the curve $T_{ijk}$ vs. $t_{jk}$ is compared against the design curve $T_i$ vs. d at $\lambda_m$ from 502 and 503, and the time $t_{jk}$ at which the layer should be terminated is computed. When the measured time t reaches $t_{jk}$, the deposition for the optically monitored layer i is terminated.

After deposition of the current layer i has completed, the apparatus 400 of FIG. 4 is reconfigured at 521 to start depositing the material associated with layer i+1, and the process loops back to 506. However, if all layers of the filter have been deposited, the LWP filter is complete, and processing stops at 522.

Figure 6A:
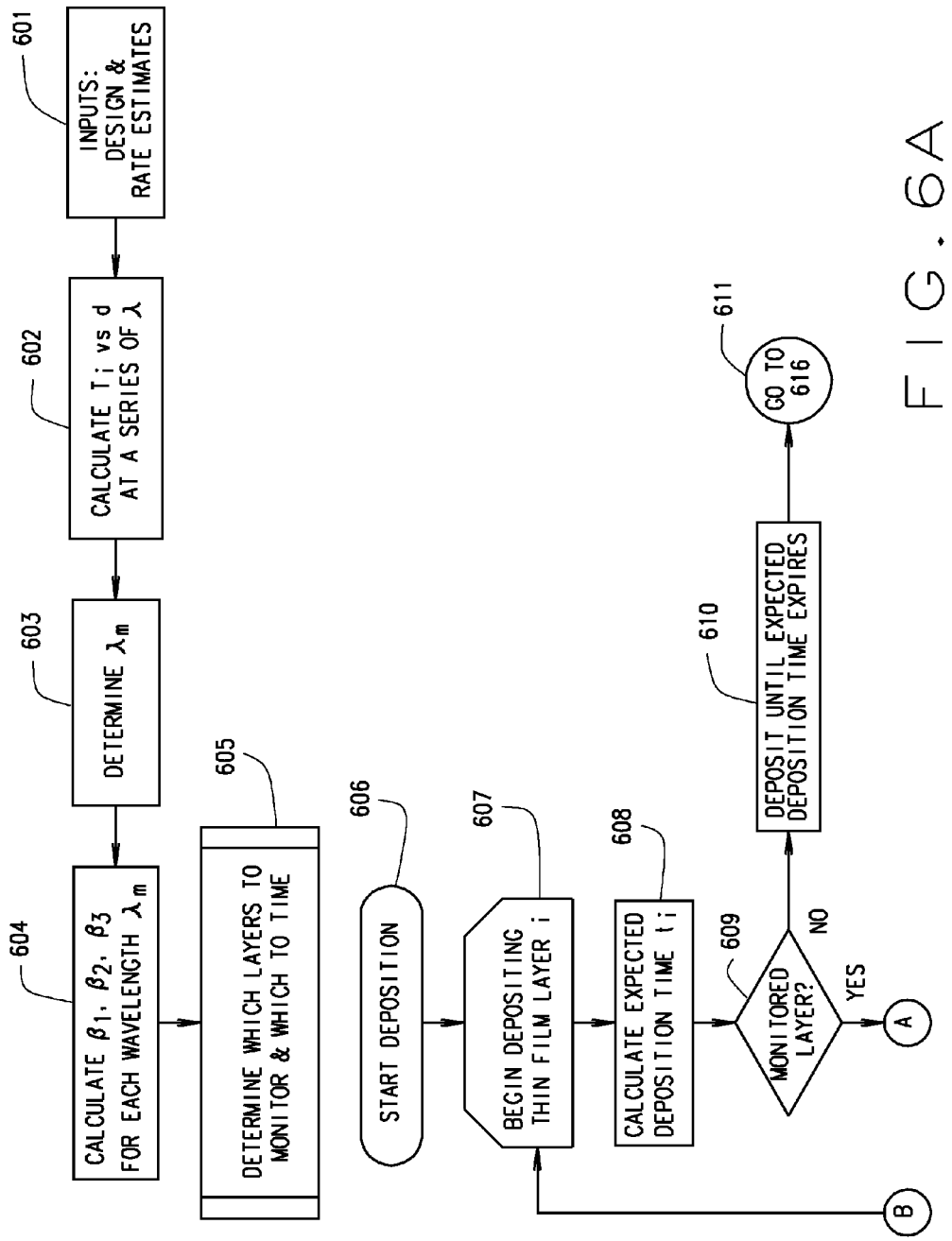
FIGS. 6A and 6B illustrate a process flow chart for making the short-wave pass component of a filter.
Figure 6B:
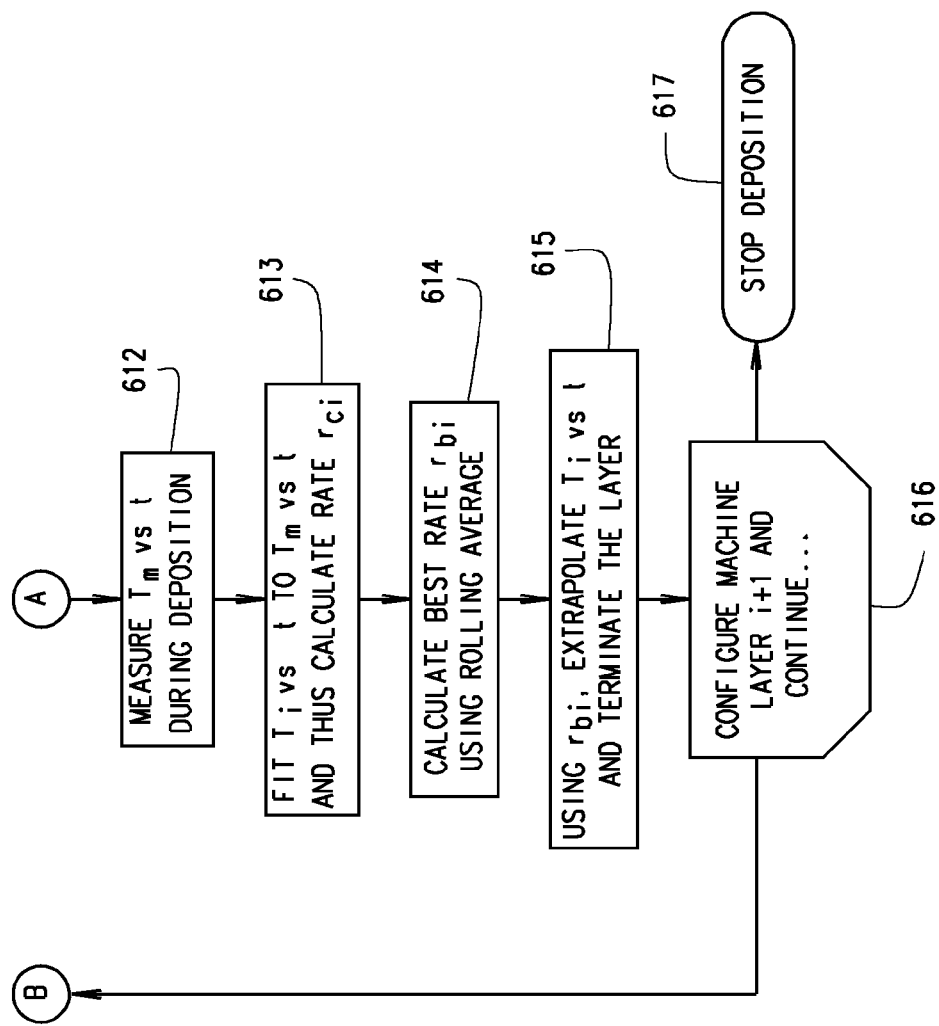

FIGS. 6A and 6B illustrate the process flow executed by the data processor 414 when manufacturing a short-wave-pass ("SWP") filter component. The process illustrated with FIGS. 6A and 6B is based on the inventor's observation that the inverse of the monitoring trace (i.e., the transmission of the monitoring light as a function of time) within each layer follows a sinusoidal pattern. As will be shown, four parameters, $\beta_1$, $\beta_2$, $\beta_3$, and $\theta_{m+1}$ are needed to fully describe the behavior of the monitoring trace for each layer in the absence of appreciable absorption, whereas a fifth parameter, D, must be included when such absorption is present, as is true for the UV filters of the present invention.

Assume initially that at the monitoring wavelength the incident medium, deposited materials, and substrate are all lossless (practically true in many, but not all, cases). At normal incidence, each layer may be described by its characteristic matrix:

$$\begin{bmatrix} \cos\theta & -i\sin\theta/n \\ -in\sin\theta & \cos\theta \end{bmatrix} \qquad \text{Eqn. (1)}$$

where n is the refractive index of the layer; $\theta$ is the accumulated phase within the layer, and i in equations 1 through 8 (and only in these equations) is the square root of −1, or $i = \sqrt{-1}$. (It should be noted that although this specification is described in the context of light striking a filter at normal incidence, one skilled in the art will appreciate that this invention also applies to polarized light striking a filter at non-normal incidence.) θ is expressed as:

$$\theta = \frac{2\pi}{\lambda_m} nd \qquad \text{Eqn. (2)}$$

where d is the metric thickness of the layer and $\lambda_m$ is the monitoring wavelength. Assuming an assembly of m layers have already been deposited, the transmission of the monitoring light within the $(m+1)^{st}$ layer, the present layer, may be expressed as:

$$T = \frac{4n_a n_s}{H} \qquad \text{Eqn. (3)}$$

where T is the level of monitoring signal within the present layer (transmission), and $n_a$ and $n_s$ are the refractive indices of the incident medium and substrate, respectively. H is defined as:

$$H = \beta_1 + \beta_2 \cos(2\theta_{m+1}) + \beta_3 \sin(2\theta_{m+1}) \qquad \text{Eqn. (4)}$$

$\beta_1$, $\beta_2$, and $\beta_3$, are defined as:

$$\beta_1 = \frac{n_a^2 + n_{m+1}^2}{2}\left(|p|^2 + \frac{|q|^2}{n_{m+1}^2}\right) + 2n_a \mathrm{Re}(pq^*) \qquad \text{Eqn. (5)}$$

where Re(pq*) is the Real Part of the product of the complex number p and the complex conjugate of the complex number q. p and q are defined in equation (8) below.

$$\beta_2 = \frac{n_a^2 + n_{m+1}^2}{2}\left(|p|^2 - \frac{|q|^2}{n_{m+1}^2}\right) \qquad \text{Eqn. (6)}$$

$$\beta_3 = \left(\frac{n_a^2}{n_{m+1}} - n_{m+1}\right)\mathrm{Im}(p*q) \qquad \text{Eqn. (7)}$$

Im(p*q) is the Imaginary Part of the product of the complex conjugate of the number p and the complex number q. p and q are defined as:

$$\begin{bmatrix} p \\ q \end{bmatrix} = \prod_{l=1}^{m}\begin{bmatrix} \cos\theta_l & \left(\frac{-i\sin\theta_l}{n_l}\right) \\ -in_l\sin\theta_l & \cos\theta_l \end{bmatrix}\begin{bmatrix} 1 \\ n_s \end{bmatrix} \qquad \text{Eqn. (8)}$$

where $\theta_l$ is accumulated phase in the $l_{th}$ layer.

For monitoring wavelengths in the UV between 220 and 320 nm, the incident medium (vacuum or air) can be assumed to be lossless but the deposited materials for the thin-film layers and substrate exhibit absorption with losses due to a non-zero extinction coefficients in imaginary parts of their respective refractive indices. For this reason, the in-situ optical monitoring algorithm is advantageously modified with an envelope slope factor to model the in-situ degradation of transmission monitoring signal (T) vs. optical thickness as well as the modification of the algorithmic fitting parameters to include calculated effects of substrate absorption and material absorption of the depositing film layers and the previously deposited back-side thin-film stack.

Specifically, the right hand expression in Equation (4) is modified to be:

$$H = [\beta'_1 + \beta'_2 \cos(2\theta_{m+1}) + \beta'_3 \sin(2\theta_{m+1})]/[1+D\theta_{m+1}] \qquad \text{Eqn. (9)}$$

where D is an additional in-situ fitted parameter used to model the decrease in transmission due to extinction in the UV for the in-situ depositing layers (taken to be front-side thin-film stack without loss of generality), substrate, and, if applicable, the previously deposited back-side thin film stack.

Further β'1, β'2, and β'3 are given by $$\beta'_1 = \left[\beta_1 \delta + (1-\alpha)^2 \frac{R_{bR}}{T_b}\right]/(1-\alpha) \qquad \text{Eqn. (10)}$$

$$\beta'_2 = \beta_2 \frac{\delta}{1-\alpha} \qquad \text{Eqn. (11)}$$

$$\beta'_3 = \beta_3 \frac{\delta}{1-\alpha} \qquad \text{Eqn. (12)}$$

Here $\beta_1$, $\beta_2$, and $\beta_3$ are defined as in equations 5, 6, and 7, and the constant $$\delta = \gamma + (2\alpha - \alpha^2)\frac{(1-A_{fR})R_{bR}}{T_b} \qquad \text{Eqn. (13)}$$

Where $T_b$ is the transmittance through the previously deposited back-side thin film stack, $R_{bR}$ is the substrate to back-side reflectance, $A_{fR}$ is the absorption of the front side stack, and α is the substrate single-pass absorption. The constant γ is given by:

$$\gamma = 1 + \frac{A_{fR}R_{bR} + A_{bR}}{T_b} \qquad \text{Eqn. (14)}$$

where $A_{bR}$ is the back-side thin film stack absorption.

Based on the above equations, the relationship between the monitoring trace T and the accumulated phase $\theta_{m+1}$ within the present layer is established. The inverse of the monitoring trace is sinusoidal, as demonstrated by the expression for H. Further, only five parameters, $\beta_2$, $\beta_2$, $\beta_3$, $\theta_{m+1}$, and D are needed to fully describe the behavior of the monitoring trace in the present layer. Because the thickness d=r×t, where r is the deposition rate and t is the deposition time, a relationship between T and r or t is also established. If the deposition rate is constant, the accumulated phase $\theta_{m+1}$ is proportional to the deposition rate. Therefore, during the deposition process, the deposition rate may be retrieved with high accuracy by fitting the in-situ measurement of the monitoring trace to the five parameters.

With this groundwork, the process of FIGS. 6A and 6B will now be described in greater detail. However, prior to initiating the process FIGS. 6A and 6B, a design for the SWP filter component is prepared. The process of designing a SWP edge filter is very similar to that of the LWP filter, with several exceptions. First, the initial structure is (0.5 L H 0.5 L)^N. Second, the shorter wavelength edge of the QW stopband should be aligned with the desired cutoff wavelength. Third, if the first layer next to the substrate is a low index layer, it should be removed.

With the design of the SWP filter at hand, the design data, as well as deposition rate data are received as input at 601. The input data has the content and format described with reference to 501 in FIG. 5A. At 602, the transmission curves $T_i$ vs.

d at a series of wavelengths for each $i^{th}$ layer are calculated as described with reference to 502 in FIG. 5A. Choosing the best monitoring wavelength $\lambda_m$ at 603 is similar to that described with reference to 503 in FIG. 5A, except that it may be more advantageous to select $\lambda_m$ by taking an average of a series of wavelengths than it is for an LWP filter.

At 604, the β parameters are calculated for each layer at wavelength $\lambda_m$ using equations (1) through (8) described above. At 605, a determination is made as to which layers should have their deposition duration controlled by optical monitoring and which layers should have their deposition duration timed using an expected deposition time $t_i$. Such determination is made by simulating the deposition of each layer and selecting the layers having the least amount of simulated error to be optically monitored. Deposition of the other layers will be timed using the expected deposition time $t_i$.

The simulation process occurs by executing the processes of 606 to 617 as described below. However, actual deposition does not occur at 606 and 607, the processing described at 609 is skipped, and instead of measuring $T_m$ vs. t at 612, it is generated. $T_m$ vs. t is generated by adding random noise to the theoretical data $T_i$ vs. d at $\lambda_m$ from 602 and 603. In the exemplary embodiment, 0.2% peak-to-peak random noise is used, and the maximum amount of error ("threshold") to select a layer for optical monitoring is to have no more than about 0.5% error from the theoretical resulting thickness $d_i$. The error calculation, in this regard, is described in more detail below with reference to 613. The layers that are simulated to exceed the threshold amount of error are flagged to have their deposition duration controlled by the best estimate of the deposition rate $r_i$ for that layer or from an average of the rates of the previous layers of like material (typically 10 to 20 such layers).

Having determined which layers are to be optically monitored at 605, deposition begins at 606. In particular, a substrate is loaded into the deposition apparatus 400, the apparatus 400 is pumped down to vacuum, and deposition of the first layer (current layer i) is initiated at 607. At 608, the expected deposition time $t_i$ for layer i is calculated as the desired thickness $d_i$ divided by the estimated deposition rate for the layer $r_i$ or from an average of the rates of the previous layers of like material. It should be noted, however, that calculation of the expected deposition time $t_i$ at 608 may be calculated prior to beginning actual deposition of the current layer i at 607.

At 609 it is determined whether the current layer i was identified as an optically monitored layer at 605. If not, deposition occurs until the expected deposition time $t_i$ expires, and the deposition apparatus is configured for deposition of the next layer, as shown at 610, 611, and 616. If it is determined that the current layer i is an optically monitored layer at 609, the transmission $T_m$ of the current layer is measured at 612 as a function of actual time t transpired, thereby producing a measured curve $T_m$ vs. t, until about 95% of time $t_i$ has elapsed. Once about 95% of the time $t_i$ has elapsed, a new layer time is calculated at 613 to 615.

To elaborate, at 613, $T_i$ vs. t (where t=d/r and $T_i$ vs. d at $\lambda_m$ was calculated and selected at 602 and 603, respectively) is fit to the measured curve $T_m$ vs. t from 612. The $T_i$ vs. t curve is fit to the measured curve $T_m$ vs. t by using a function that minimizes the error between the two curves by varying $\beta_1$, $\beta_2$, $\beta_3$, and the deposition rate r. An example of such a function is the Levenburg-Marquardt method implemented under the name "mrqmin( )" in the book Numerical Recipes in C: The Art of Scientific Computing, by Press, W. H.; Teukolsky, S. A.; Vetterling, W. T.; and Flannery, B. P., 2nd ed., Cambridge University Press, Cambridge, 1995. These calculations result in a calculated deposition rate for the current layer i, or $r_{ci}$.

Because of noise in the overall system and the sensitivity of the high-performance SWP filters to small layer-thickness errors, the calculated rates $r_{ci}$ tend to be insufficiently accurate if used directly. Therefore, a "best rate" for each layer, $r_{bi}$, is calculated at 614 as the average of the calculated rate $r_{ci}$ and calculated rates $r_{cj}, r_{c,j+2}, \ldots, r_{c,i-4}, r_{c,i-2}$ for a certain number (i−j)/2 of previous layers of the same material. In other words, the best rate is a rolling average of the current and previous rates from layers of like material within a certain window. Typically, this window includes about 20 layers.

At 615, the best rate $r_{bi}$ is used to calculate the layer termination time $t_t=d/r_{bi}$, and the layer is terminated when the clock reaches this time. Once deposition of the current layer is complete, the deposition apparatus 400 of FIG. 4 is reconfigured at 616 to start depositing the material associated with the next layer i+1, and the process loops back to 607. However, if all layers have been deposited, manufacturing of the SWP filter is complete, and the process ends at 617.

The improved filters have the general structure schematically illustrated in FIG. 3 but are made by the processes described herein in connection with FIGS. 5 and 6. In essence, the filters comprise a transparent substrate advantageously having a pair of optically flat planar major surfaces and a plurality of alternating layers of relatively high index and relatively low index materials. The materials are hard oxide coating materials such as $SiO_2$, $Ta_2O_5$, $Nb_2O_5$, $HfO_2$, $TiO_2$, and $Al_2O_5$.

The filters differ from filters described in the '430 patent in that the effect of absorption is accounted for in the design and fabrication. They differ from pre-430 patent conventional filters primarily in the number of layers (more than 30 and typically more than 100) and in that the thicknesses of layers deposited are controlled by the processes of FIGS. 5 and 6 to produce a highly sloped steep edge (edge steepness may be as low as about 0.8% or lower). The edge steepness, in this regard, is measured by dividing (a) the edge width from the 50% transmission wavelength to the optical density 6 ("OD6") wavelength by (b) the 50% transmission wavelength. Accordingly, lower steepness values indicate greater slope. Optical density ("OD") is a measure of the blockage encountered by impinging light and is defined as follows:

$$OD = -\log_{10}(T) \qquad \text{Eqn. (15)}$$

where T is the transmittance having a value between zero and one. OD6 therefore corresponds to a transmittance of $10^{-6}$. Advantageously the edge steepness, as defined above, may be less than about 0.58% at 266 nm and 0.78% at 248 nm. However, the edge steepness may be increased if necessary.

In addition, the filters so made exhibit an average transmission well above 40% within the operating range of the passband between 230 and 320 nm. Average transmission of the filters typically exceeds 90% in the operating range greater than 320 nm. The filters thus provide performance exceeding that of the highest performing conventional soft-coating filters with a more robust and durable hard-coated structure.

The invention can now be more clearly understood by consideration of the following example: a UV band transmission filter with extended out-of-band blocking was made employing the design and fabrication process described above. The filter was designed to transmit a band of wavelengths within the range of 230 to 320 nanometers and to provide extended blocking. The substrate was a fused silica plate of thickness 2 mm having a pair of optically smooth planar major surfaces. The LWP and SWP filter components were formed on the respective major surfaces. The filter components comprised stacks of silica and hafnia layers of substantially quarter wave thickness deposited as described herein. To reduce UV absorption the flow of $O_2$ was controlled during deposition of both silica and hafnia and the assist ion beam used during the deposition of silica was turned off during the deposition of hafnia. The deposition algorithms were modified as described herein to account for the absorption of UV light by the hafnia layers. The thicknesses in the exemplary filters are set forth in Appendix A. The layers are counted from the substrate outward toward air.

FIG. 7 shows the measured and theoretical transmission spectra of the resulting filter. Curve 1 is the measured spectrum, and curve 2 is the theoretical spectrum.

FIG. 8 illustrates the optical density (OD) spectrum of the resulting filter. Curve 1 is the measured spectrum, and curve 2 is the theoretical spectrum. The OD is a measure of the blockage encountered by impinging light. As previously noted, the out-of-band blocking for this UV band transmission filter extends through the visible spectrum. For all wavelengths in the range 230 to 600 nanometers, the filter provides an average optical density of 3 or more. Indeed, the exemplary filter provides an average optical density of 3 or more for the range 230 to 840 nanometers. Here average optical density (called $OD_{avg}$) is defined as $$OD_{avg} = \frac{1}{\lambda_2 - \lambda_1} \int_{\lambda_1}^{\lambda_2} \text{Min}[-\log_{10}(T(\lambda)), 6] d\lambda \quad \text{Eqn. (16)}$$

Where Min[a,b] is mathematical notation to indicate that the smaller of the values a and b is to be chosen. The filter also provides an optical density of the average transmission over the wavelength range 320 to 700 nm of greater than 4. Here the optical density of the average transmission (called $OD(T_{avg})$) is defined as $$OD(T_{avg}) = -\log_{10}\left[\frac{1}{\lambda_2 - \lambda_1}\int_{\lambda_1}^{\lambda_2} T(\lambda) d\lambda\right] \quad \text{Eqn. (17)}$$

The resulting exemplary filter is believed to have characteristics superior to any currently available commercial UV fluorescence filter. It provides transmission up to three or more times greater, edge slopes up to four times sharper, and deep extended out-of-band blocking into and even through the visible range.

Because of the superior characteristics of the filter, superior optical analysis systems can be built. Such a system, as described above, would include a source of excitation light for exciting a sample, a filter in accordance with the invention between the source and the sample and a collection light path from the sample.

While we have exemplified our method and resulting filter as a transmission filter having coatings to produce a low pass filter and a high pass filter on opposing surfaces of a substrate, it should be clear that the same method can be used to fabricate a transmission filter where both coatings (low pass and high pass) are stacked on the same surface of the substrate. The method can also be used to fabricate a transmission filter on one surface of the substrate by hard coatings that form a multi-cavity Fabry-Perot transmission filter. If the coatings are stacked on one surface, the opposing surface can be coated for anti-reflection or to extend blocking of out-of-band wavelengths.

It now can be seen that in one aspect the invention is an optical bandpass filter for transmitting a passband of ultraviolet light. The filter comprises a substrate having one or more surfaces for supporting thin film coatings, a plurality of alternating layers of at least two hard-coating materials of higher refractive index and lower refractive index overlying at least one of the surfaces to form a transmission filter. The passband of the filter is a band of ultraviolet light within the range of 230 nanometers to 320 nanometers, i.e. the transmission band of the filter falls within, encompasses or partially overlaps the 230 to 320 nanometer range. The filter has an average transmission of light over the passband exceeding 40% and an average optical density of at least 3.0 at all wavelengths over the range 230 to 600 nanometers and preferably at least 3.0 over the range 230 to 840 nanometers.

The bandpass filter can comprise a long wave pass filter component and a short wave pass filter component that overlie respective opposing surfaces of the substrate. Alternatively, the long wave pass filter component and the short wave pass filter component can overlie the same surface of the substrate. Or the bandpass filter can comprise a plurality of alternating layers on at least one surface of the substrate forming a multi-cavity Fabry-Perot transmission filter.

In another aspect, the invention comprises an improved optical analysis system comprising a source of excitation light for exciting a sample, an excitation filter between the source and the sample, and a collection light path from the sample. In the improved system, the light source comprises an ultraviolet light source and the excitation filter comprises a filter as described herein.

Yet another aspect of the invention is an improved method of making an optical bandpass filter for transmitting a band of light with extended out of band blocking. The method comprises the steps of providing a substrate having one or more surfaces and forming on one or more surfaces a transmission filter comprising alternating layers of at least two hard coating materials of higher refractive index and lower refractive index. Each of the layers are deposited by a data processor controlled process comprising calculating with the data processor a theoretical transmission $T_i$ of light through the layer, calculating with the data processor an expected deposition time $t_i$ of the layer, measuring during the deposition of the layer for a period of time less then $t_i$ a measured transmission $T_m$ of light through the layer and determining with the data processor when deposition of the layer is to terminate based upon the theoretical transmission $T_i$ and the measured transmission $T_m$. In the improved process, the calculations of $t_i$ ant $T_i$ accounts for absorption by the relation of Equations (9) thru (14) herein.

The present disclosure can be embodied in-part in the form of computer-implemented processes and apparatuses for practicing those processes. The present disclosure can also be embodied in-part in the form of computer program code containing instructions embodied in tangible media, such as floppy diskettes, CD-ROMs, hard drives, or an other computer readable storage medium, wherein, when the computer program code is loaded into, and executed by, an electronic device such as a computer, micro-processor or logic circuit, the device becomes an apparatus for practicing the present disclosure.

The present disclosure can also be embodied in-part in the form of computer program code, for example, whether stored in a storage medium, loaded into and/or executed by a computer, or transmitted over some transmission medium, such as over electrical wiring or cabling, through fiber optics, or via electromagnetic radiation, wherein, when the computer program code is loaded into and executed by a computer, the computer becomes an apparatus for practicing the present disclosure. When implemented in a general-purpose microprocessor, the computer program code segments configure the microprocessor to create specific logic circuits.

As various changes could be made in the above constructions without departing from the scope of the disclosure, it is intended that all matter contained in the above description or shown in the accompanying drawings shall be interpreted as illustrative and not in a limiting sense.

The invention claimed is:

1. A method of making an optical bandpass filter for transmitting a band of ultraviolet light within the range of 230 nanometers to 320 nanometers and with extended out-of-band blocking comprising the steps of:
   providing a substrate having front-side and backside surfaces;
   forming a transmission filter on at least one of said surfaces, said transmission filter consisting of alternating layers of at least two hard coating materials of a higher refractive index and a lower refractive index respectively;
   wherein each individual layer of the alternating layers is deposited by a data processor controlled process comprising the steps of:
   calculating with the data processor, a theoretical transmission ($T_t$) of ultraviolet light through the individual layer,
   calculating with the data processor an expected deposition time ($t_i$) of the individual layer,
   measuring, during the deposition of the individual layer for a period of time less than ($t_i$), a measured transmission ($T_m$) of light through the layer,
   determining with the data processor when deposition of the individual layer is to terminate based upon the theoretical transmission ($T_t$) and the measured transmission ($T_m$); and
   wherein the calculation of ($t_i$) and ($T_t$) accounts for absorption of ultraviolet light by the layer by defining the transmission of UV light within the individual layer as $$T = \frac{4n_a n_s}{H}$$

where T is a level of a monitoring signal within the individual layer,
where $n_a$ and $n_s$ are the refractive indices of the individual layer and substrate, respectively,
where H is defined as $$H = [\beta_1' + \beta_2' \cos(2\theta_{m+1}) + \beta_3' \sin(2\theta_{m+1})] / [1 + D\theta_{m+1}]$$

with $$\beta_1' = \left[\beta_1 \delta + (1-\alpha)^2 \frac{R_{bR}}{T_b}\right] / (1-\alpha)$$

$$\beta_1 = \frac{n_a^2 + n_{m+1}^2}{2}\left(|p|^2 + \frac{|q|^2}{n_{m+1}^2}\right) + 2n_a \text{Re}(pq^*)$$

$$\beta_2' = \beta_2 \frac{\delta}{1-\alpha}$$

$$\beta_2 = \frac{n_a^2 - n_{m+1}^2}{2}\left(|p|^2 + \frac{|q|^2}{n_{m+1}^2}\right)$$

$$\beta_3' = \beta_3 \frac{\delta}{1-\alpha}$$

$$\beta_3 = \left(\frac{n_a^2}{n_{m+1}} - n_{m+1}\right)\text{Im}(p*q)$$

$$\delta = \gamma + (2\alpha - \alpha^2)\frac{(1-A_{fR})R_{bR}}{T_b}$$

$$\gamma = 1 + \frac{A_{fR}R_{bR} + A_{bR}}{T_b}$$

where Re(pq*) is a real part of a product of a complex number p and a complex conjugate of a complex number q, defined as $$\begin{bmatrix} p \\ q \end{bmatrix} = \prod_{l=1}^{m} \begin{bmatrix} \cos\theta_l & \left(\frac{-i\sin\theta_l}{n_l}\right) \\ -in_l\sin\theta_l & \cos\theta_l \end{bmatrix} \begin{bmatrix} 1 \\ n_s \end{bmatrix}$$

where $\theta_l$ is an accumulated phrase in an $l^{th}$ deposited layer,
where D is an in-situ fitted parameter which models a decrease in transmission due to extinction in the UV spectrum for any previously-deposited layers on the front-side and backside surfaces and in the substrate,
where $T_b$ is the transmittance through any previously deposited back-side layers,
where $R_{bR}$ is the substrate to backside surface reflectance,
where $A_{fR}$ is the absorption of any previously-deposited layers on the front-side surface of the substrate,
where $\alpha$ is the substrate single-pass absorption value, and
where $A_{bR}$ is the absorption of any previously-deposited layers on the backside surface of the substrate.

2. The method of claim 1 wherein at least a portion of said alternating layers form a short wave pass filter component.

3. The method of claim 1 wherein the alternating layers form a multi-cavity Fabry-Perot filter.

4. The method of claim 1 wherein the at least two hard coating materials include silica and hafnia.

5. The method of claim 4 wherein the silica and hafnia are deposited by sputtering.

6. The method of claim 5 wherein the silica is deposited by ion beam assisted sputtering and the hafnia is deposited by sputtering without ion beam assistance.

7. The method of claim 6 wherein the sputtering is conducted in an $O_2$ ambient environment with a rate of injection of $O_2$ chosen to reduce ultraviolet light absorption by the deposited layers.

8. A method of making an optical bandpass filter on at least one surface of a substrate for transmitting a passband of ultraviolet light with extended out-of-band blocking comprising the steps of:
   depositing a plurality of alternating layers of first and second hard-coating materials onto the at least one surface of the substrate, said first and second hard-coating materials having different refractive indices;
   monitoring a measured transmission ($T_m$) of ultraviolet light through a selected subset of said plurality of alternating layers during said step of deposition;
   wherein said step of depositing each of said plurality of layers requires:
   a. calculating a theoretical transmission ($T_t$) of ultraviolet light through said layer based on a model of transmission accounting for absorption at ultraviolet wavelengths;
   b. calculating an expected deposition time ($t_i$) of said layer; and c. beginning a deposition of said layer onto said substrate surface for a first deposited layer, or onto an immediately preceding layer of deposited material;

wherein said step of depositing for each of said plurality of layers excluded from said selected subset of monitored layers continues for said expected deposition time ($t_i$); and wherein said step of depositing, for each of said plurality of layers included in said selected subset of monitored layers, further includes the steps of a. measuring, during deposition of each of said selected layers, at a point in time less than ($t_i$), a transmission ($T_m$) of ultraviolet light through said selected layer together with said substrate and each of said previously deposited alternating layers;

b. establishing a termination point in time for said deposition of said selected layer, responsive to said theoretical transmission ($T_i$), said measured transmission ($T_m$), and to absorption of ultraviolet light by said selected layer together with said substrate and each of said previously deposited alternating layers; and c. continuing said deposition of said selected layer until reaching said established termination point in time.

9. The method of claim 8 wherein said step of depositing forms a first interference filter component and a second interference filter;

wherein said first interference filter component is a long wavelength pass filter that transmits the passband UV wavelengths while blocking wavelengths below the passband UV wavelengths; and wherein said second interference filter component is a short wavelength pass filter that transmits the passband UV wavelengths while blocking wavelengths above the passband UV wavelengths.

10. The method of claim 8 further including the step of annealing said deposited layers;

wherein said annealing alters said indices of refraction of said first and second hard-coating materials; and wherein said step of establishing a termination point in time for said deposition of said selected layer accounts for said alteration of an index of refraction by said step of annealing.

11. The method of claim 8 wherein a wavelength of said ultraviolet light is within the range of 230 nanometers to 320 nanometers.

12. The method of claim 8 wherein said step of establishing a termination point in time for said deposition of said selected layer is further responsive to absorption of ultraviolet light by said substrate and each previously-deposited layer of material on said substrate.

13. The method of claim 8 wherein said step of depositing a plurality of alternating layers of first and second hard-coating materials results in the deposition of at least 30 discrete layers onto said substrate.

14. The method of claim 8 wherein said plurality of alternating layers of first and second hard-coating materials are deposited by ion-beam sputtering deposition.

15. The method of claim 14 wherein said first material is hafnia, and wherein said second material is silica.

16. The method of claim 15 further including the step of bombarding the substrate surface with an assist ion beam during deposition of said silica.

17. The method of claim 14 further including the step of injecting a controlled a flow of $O_2$ into said first and second materials during said deposition step, said controlled flow of $O_2$ altering an ultraviolet light absorption characteristic of said layer undergoing deposition.

18. The method of claim 8 wherein said theoretical transmission $T_i$ of ultraviolet light through said layer depends sinusoidally on a thickness of said layer.

19. A method of making an optical bandpass filter on at least one surface of a substrate for transmitting a range of ultraviolet light within an limited passband and having extended out-of-band blocking, comprising the steps of:

sequentially depositing a plurality of alternating layers of first and second hard-coating materials onto the at least one surface of the substrate, said first and second hard-coating materials having different refractive indices;

during deposition of at least one of said plurality of alternating layers, evaluating a set of parameters to establish a termination point in time for said deposition of said alternating layer; and wherein said set of parameters includes a variable representative of a decrease in transmission of UV light within said passband through said layer, any in-situ layers previously deposited on said substrate, and said substrate.

* * * * *